(12) United States Patent
Yu et al.

(10) Patent No.: US 7,005,539 B2
(45) Date of Patent: Feb. 28, 2006

(54) FERULIC ACID DIMERS AND THEIR PHARMACEUTICALLY ACCEPTABLE SALTS, THEIR PREPARATION AND USE THEREOF FOR TREATING DEMENTIA

(75) Inventors: Jaehoon Yu, Seoul (KR); Kye-Jung Shin, Seoul (KR); Dong-Jin Kim, Seoul (KR); Kyung-Sik Lee, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 58 days.

(21) Appl. No.: 10/474,666

(22) PCT Filed: Dec. 5, 2001

(86) PCT No.: PCT/KR01/02103

§ 371 (c)(1),
(2), (4) Date: Apr. 8, 2004

(87) PCT Pub. No.: WO02/083625

PCT Pub. Date: Oct. 24, 2002

(65) Prior Publication Data

US 2004/0236148 A1 Nov. 25, 2004

(30) Foreign Application Priority Data

Apr. 17, 2001 (KR) ............... 2001-20411

(51) Int. Cl.
*C07C 63/33* (2006.01)
*C07C 59/48* (2006.01)
*C07C 59/40* (2006.01)
*C07C 59/42* (2006.01)

(52) U.S. Cl. ............... 562/400; 562/405; 562/465

(58) Field of Classification Search ............... 562/400, 562/405, 465
See application file for complete search history.

(56) References Cited

OTHER PUBLICATIONS

International Preliminary Examination Report for PCT/KR01/02103.*

* cited by examiner

*Primary Examiner*—Elvis O. Price
(74) *Attorney, Agent, or Firm*—Bachman & LaPointe, P.C.

(57) ABSTRACT

The present invention relates to ferulic acid dimers and their pharmaceutically acceptable salts, preparation method and use thereof for treating dementia, which have excellent effect on the learning and memory-retention ability in vivo, thus it can be use for dementia.

15 Claims, 1 Drawing Sheet

FERULIC ACID DIMERS AND THEIR PHARMACEUTICALLY ACCEPTABLE SALTS, THEIR PREPARATION AND USE THEREOF FOR TREATING DEMENTIA

TECHNICAL FIELD

The present invention relates to ferulic acid dimers and their pharmaceutically acceptable salts having excellent effect on the learning and memory-retention ability in vivo, preparation thereof and their usage of treating dementia.

BACKGROUND ART

Dementia is a degenerative brain disorder identified clinically and more than fifty percents of people seventy and over are attacked by senile dementia. Average age of people in advanced country is already close to eighty, and thus the population of elderly people suffering from dementia is increasing, and the expenses for treating and caring of them reaches astronomical figures. In Korea, the population of dementia patients has increased suddenly as the average age of the population becomes higher, and thus the treatment and management of such patients are gathering urgency as social problems.

Upon pathological examination of dementia patients' cerebral cells and organs, plaque formed by accumulation of β-amyloid protein has been commonly observed. However, no one knows that such plaque works as pathogenic or be accumulated as products of pathogenesis. Forming of senile plaque in most of dementia patients and improving dementia symptoms decreasing of plaque are observed. Many researchers have looked for the cause of dementia and its treatment method, but they have not been revealed, yet.

In many countries, Research for treating method of the diseases of unknown cause with alternative medicines or medicinal foods has been conducted. Korean Pat. Application No.19330/2000 and International Pat. Application No. PCT/KR00/19330 by the present inventors, the content thereof being incorporated herein by reference, disclose hydroxy cinnamic acid derivatives or extract from Korean angelica root containing them, in which the compound is relatively simple 4-hydroxy-3-methoxy cinnamic acid (hereinafter, referred to as ferulic acid) having the following chemical structure. The excellent therapeutic effects of ferulic acid of dementia has been confirmed by an in vivo experiment, in which separated ferulic acid monomer is administered to mouse and then memory-retention ability of mouse is considerably increased. However, a biochemical mechanism of ferulic acid has not been revealed.

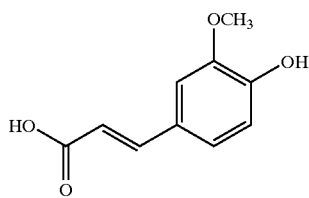

Meanwhile, transthyretin protein, present in high concentrations in the blood, is known to be a representative plaque-forming protein, and is found in the cerebrospinal medulla of dementia patients, and is a material used for amyloidosis modelling.

The transthyretin exists in a stable tetrameric structure at physiological pH condition. However, the stable tetramer is destabilized by low pH, certain point mutations, and morphological changes induced by pressure, and can be further destabilized into monomeric form, the monomers then aggregating and thus forming plaque. That is, the decomposition process of transthyretin tetramers to monomers acts as a direct cause of senile plaque-formation. Furthermore, people afflicted by familial amyloid neuropathy characterized by unstable transthyretin tetramers of mutatant form can, in severe cases, lose their life.

Hence, the concentration of tetrameric transthyretin is in inverse proportion to formation of plaque. That is to say, transthyretin proteins constitute stable tetramer, and if stable tetramers are constituted, formation of plaque is markedly decreased.

In the blood, transthyretin are stabilized by forming conjugates with 25% of the total thyroid hormone thyroxine. Thyroxine is responsible for increasing the stability of transthyretin tetramers and preventing monomers, the cause of plaque, from being formed. However, even though thyroxine prevents formation of plaque, administration with excessive amounts may cause severe side effects.

X-ray crystalline structure of the transthyretin protein and thyroxine conjugate shows that, two thyroxine molecules are formed sandwiched form between two transthyretin dimers in the tetrameric structure, the dimers showing an enantiomeric image and constructing head to head or tail to tail. X-ray crystalline structures of the transthyretin proteins are observed in various compounds containing thyroxine.

SUMMARY OF THE INVENTION

Leading to the present invention, the intensive and thorough research into novel treatments for dementia, carried out by the present inventors aiming to avoid the problems encountered in the prior arts, resulted in the finding that transthyretins are stabilized by two thyroxine molecules, and further that ferulic acid having a similar structure to thyroxine, is an effective dementia treatment, so that ferulic acid dimers in which two ferulic acids are connected via carbon chains or oxygen or nitrogen-containing chains are designed and synthesized, the obtained ferulic acid dimmers have improved treatment effect of dementia and minimizing side-effects caused by excessive administration of drugs, because of ferulic acid having no hormone properties.

Accordingly, It is an object of the present invention to provide ferulic acid dimers and their pharmaceutically acceptable salts.

It is a further object of the present invention to provide preparing method of the ferulic acid dimers.

It is an additional object of the present invention to provide use of the ferulic acid dimers as treatments for dementia.

It is an additional object of the present invention to provide intermediates of the ferulic acid dimers.

BRIEF DESCRIPTION OF THE DRAWINGS

The above and other objects, features and other advantages of the present invention will be more clearly understood from the following detailed description taken in conjunction with the accompanying drawing, in which.

Figure 1:
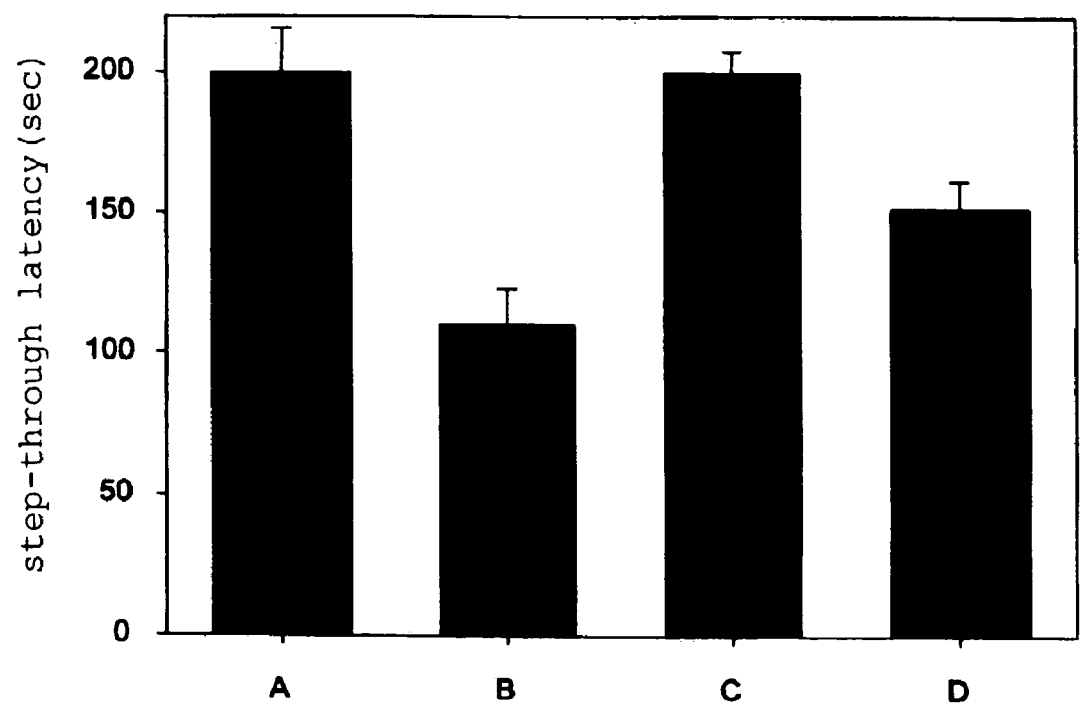
FIG. 1 is a comparing histogram showing passive avoidance response of times of ferulic acid dimmer of the present invention with passive avoidance response time of the compounds according to comparative examples.

A is mice administered with reverse phase beta-amyloid,
B is mice administered with beta-amyloid,
C is mice administered with ferulic acid dimer and beta-amyloid, and
D is mice administered with ferulic acid and beta-amyloid.

DISCLOSURE OF THE INVENTION

To accomplish these objects, the presen invention provides ferulic acid dimers represented by formula 1 and their pharmaceutically acceptable salts:

Formula 1

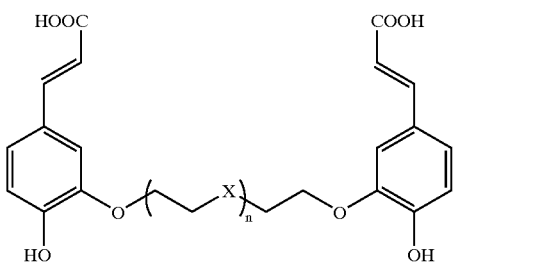

Wherein X is C, O or N, and
n is an integer of 0–3,
preferably X is C or N, and n is an integer of 0–1, and
more preferably X is C, and n is 1.

Ferulic acid dimmers of the present invention are prepared in a form of inorganic salts, such as sodium salt, potassium salt, magnesium salt and calcium salt; or in a form of organic salts with angelic acid, lysine, ethanolamine, N,N'-dibenzyl ethylenediamine and α-tocopherol. Further, ferulic acid dimers of the present invention can be prepared as ester forms with triterpene alcohol or plant sterols such as cycloartenol.

As can be seen in the formula 1, a ferulic acid dimer of the present invention retain four functional groups, which ferulic acid have had and in which methoxy groups are substituted at a meta position of each benzene ring comprising the core of each ferulic acid monomer, the benzene rings being connected through chains of suitable lengths, that is, 2–10 carbon containing chains or oxygen or nitrogen-containing chains.

In the present invention, ferulic acid dimers of formula 1 inserted between two transthyretin dimers, more specifically, homo dimers of transthyretin, in a sandwich form, stabilize transthyretin, thereby preventing conversion of transthyretin to plaque. Further, in accordance with Examples of the present invention, it is expected that the activity of synuclein and plakophilin, which are directly or indirectly related to intercelluar or intracelluar plaque formation, may be inhibited. In the Experimental Examples of the present invention, ferulic acid dimers were directly administered to the cerebral ventricle of a mouse, resulting in improvements of the learning and memory-retention ability, thus being usable to prevent and treat dementia including Alzheimer's disease, characterized by decrease of the memory-retention ability.

Also, the present invention provides the preparation method of ferulic acid dimers represented by formula 1 according to reaction scheme 1.

The preparation method of ferulic acid dimers of the present invention comprises reacting hydroxybenzaldehyde compound represented by formula 2 with malonic acid to obtain ferulic acid dimers of formula 1.

The reaction, known as in the name of "Knoevenagel reaction" is commonly and widely known in the field of organic chemistry, and the reaction conditions (usable solvents, reaction temperatures and reaction times and so forth) may be appropriately selected, considering reactants and products. In this regard, as the solvent, various alkaline organic solvents including piperidine and pyridine are can be used, and for example, lutidine, dimethylformamide and so on. Also, The reaction temperature is usally in the range of 20 to 80° C., and the reaction time ranges commonly from 2 to 6 hours. It is preferred that the reaction is conducted at 40–60° C. for 3–5 hours in the presence of piperidine and pyridine.

Reaction scheme 1

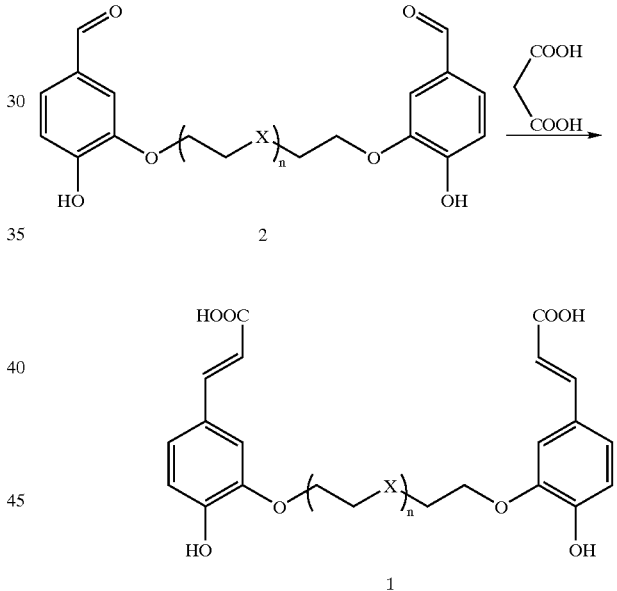

Wherein X is C, O or N, and
n is an integer of 0–3,
preferably, X is C or N, and n is an integer of 1, and
more preferably, X is C, and n is 1.

In order to prepare ferulic acid dimers of the present invention, hydroxybenzaldehyde of formula 2 used as a starting material can be produced according to method shown in the following reaction scheme 2. More specifically, this can be obtained according to following steps, a hydroxybenzaldehyde compound of formula 4 is reacted with a ditosyl compound of formula 5 in the presence of base to obtain an aldehyde compound of formula 3, which is then treated with an acidic solution and thus deprotected, to produce a hydroxybenzaldehyde compound of formula 2.

Reaction scheme 2

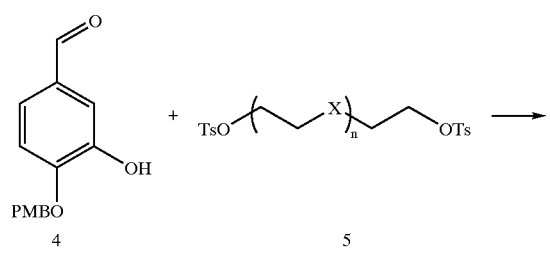

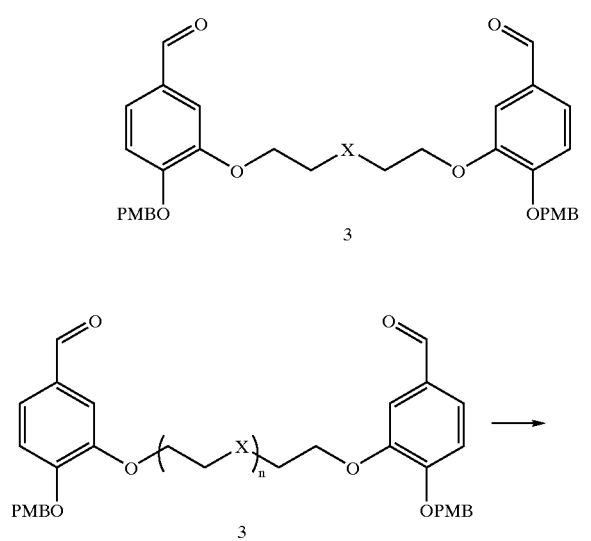

Wherein X is C, O or N, and
n is an integer of 0–3,
preferably, X is C or N, and n is an integer of 0–1, and more preferably, X is C and n is 1.
PMB is paramethoxybenzyl groups.

In the preparation method, examples of the useful bases include LiH, NaH, KH and the like, but are not certainly limited to. In addition, the bases in which hydrogen atoms can be isolated from hydroxy groups in acidic benzene rings may be used and are not specifically restricted. The acids used for deprotection comprise hydrochloric acid, sulfuric acid, nitric acid, etc and preferably hydrochloric acid is used.

The present invention provides the intermediates represented by formulas 2 and 3, used in the preparation of ferulic acid dimers represented by formula 1.

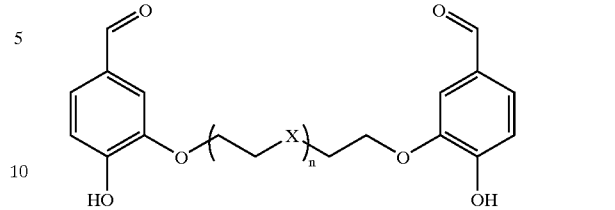

Formula 2

Wherein X is C, O or N, and n is an integer of 0–3, preferably, X is C or N, and n is an integer of 0–1, and more preferably, X is C, and n is 1.

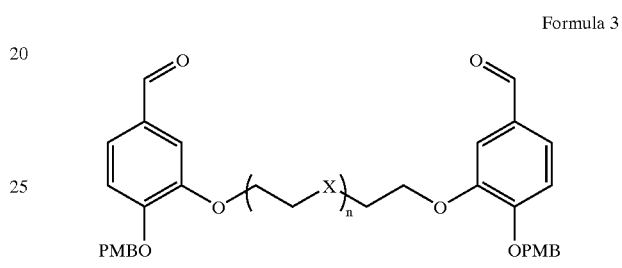

Formula 3

Wherein X is C, O or N, and n is an integer of 0–3, preferably, X is C or N, and n is an integer of 0–1, and more preferably, X is C, and n is 1. PMB is paramethoxybenzyl group.

According to the general methods, ferulic acid dimers of formula 1 can be mixed with suitable carriers or vehicles, or diluted with diluents to produce pharmaceutical compositions for treating dementia. Suitable carriers, vehicles and diluents comprise lactose, dextrose, sucrose, sorbitol, mannitol, xylitol, erythritol, maltitol, starches, acacia gum, alginates, gelatin, calcium phosphate, calcium silicate, cellulose, methylcellulose, microcrystalline cellulose, polyvinylpyrolidone, water, methyl hydroxy benzoates, propylhydroxybenzoates, talc, magnesium stearate and mineral oil. The pharmaceutical compositions further comprise fillers, antiagglutinating agents, lubricants, wetting agents, flavors, emulsifiers, preservatives, etc. The compositions of the present invention for administeration to mammals can be prepared in the dosage form using methods well known in the art to provide fast, continuous or sustained release of active ingredients. The dosage form may be a tablet, pill, powder, sachet, elixir, suspension, emulsion, solution, syrup, aerosol, soft or hard gelatin capsule, sterile injectable solution, or sterile packaged powder.

The pharmaceutical composition of the present invention may be administered through various routes including oral, or by transdermal, subcutaneous, intravenous or intramuscular introduction. Typical daily doses may range from 10 to 30 mg/kg in the body weight, and they can be administered in a single dose or in divided doses. However, it should be understood by anyone skilled in the art that the amount of the active ingredient actually administered ought to be determined in light of various relevant factors including the chosen route of administration, the age, sex and body weight of the individual subject, and the severity of the subject's symptoms; and therefore, the above dose should not be construed to limit the scope of the present invention in any way. Ferulic acid dimers of ther present invention do not show acute toxicity in the rat test and do not cause side-effects in terms of liver function.

EXAMPLE

Example 1

Synthesis of 1,2-[2-(para-methoxy-5-(carboxylvinyl))]phenoxyethane (Step 1) Synthesis of 1,2-[2-(para-methoxybenzyloxy)-5-formyl]phenoxyethane 10 g(38.7 mmol) of 4-(para-methoxybenzyloxy)-3-hydroxybenzaldehyde was dissolved in 200 ml of absolute dimethylformamide, and then 1.55 g(38.7 mmol) of 60% NaH was slowly added at room temperature. The reaction mixture was stirred at this temperature for 30 minutes, after which 7.17 g(19.4 mmol) of ethyleneglycol ditosylate was added after certifying the generation of gas had been stopped. The reaction mixture was stirred at 30° C. for 48 hours, and then the completion of reaction was confirmed by use of thin layer chromatography(TLC), followed by adding the reaction mixture with 3000 ml of water and vigorously stirring. The produced solid compound was filtered, washed with 2000 ml of water and 1000 ml of hexane, and then dried in a vacuum dryer, to yield 9.25 g(87.9%) of 1,2-[2-(para-methoxybenzyloxy)-5-formyl]phenoxyethane, as light brown solid.

$^1$H NMR(300 MHz, DMSO): δ 9.79 (s, 2H), 7.52 (d, 2H, J=8.25 Hz), 7.49 (s, 2H), 7.31 (d, 4H, J=8.52 Hz), 7.24 (d, 2H, J=8.25 Hz), 6.83 (d, 4H, J=8.52 Hz), 5.11 (s, 4H), 4.20 (s, 4H).

(Step 2) Synthesis of 1,2-(2-hydroxy-5-formyl)phenoxyethane 6.87 g(12.6 mmol) of the compound of formula 3, prepared in the step 1, was dissolved in 250 ml of ethanol, and then 100 ml of 1 N aqueous hydrochloric acid solution was added, The reaction heated to reflux for 2 hours. After the completion of reaction was confirmed using thin layer chromatography, the reaction mixture was concentrated under reduced pressure and added with 500 ml of water. The produced solid was filtered, washed with 500 ml of water and 500 ml of hexane, and then dried in a vacuum dryer, to obtain 3.7 g(97%) of 1,2-(2-hydroxy-5-formyl)phenoxyethane as pale yellow solids.

$^1$H NMR (300 MHz, DMSO): δ 9.78 (s, 2H), 7.49 (d, 2H, J=1.74 Hz), 7.44 (dd, 2H, J=1.74, 8.06 Hz), 6.99 (d, 2H, J=8.06 Hz), 4.42 (s, 4H).

(Step 3) Synthesis of 1,2-[2-hydroxy-5-(2-carboxyvinyl)]phenoxyethane 1 g(3.31 mmol) of the compound of formula 2, prepared in the step 2, and 1.38 g(13.2 mmol) of malonic acid were fully dissolved in 27 ml of absolute pyridine, and then added with 1.01 ml of piperidine. The reaction mixture was stirred at 50° C. for 4 hours, and then cooled at room temperature after the completion of reaction had been confirmed, followed by filtering the produced crystals. The crystals were dissolved in water and added with 2 N aqueous hydrochloric acid solution until acidic pH was obtained. the obtained crystals were filtered, washed with 200 ml of water and dried in the vacuum dryer, to obtain 0.67 g(52.4% yield) of 1,2-[2-hydroxy-5-(2-carboxyvinyl)]-phenoxy ethane as white crystals.

$^1$H NMR (300 MHz, DMSO): δ 12.2 (bs, 2H), 9.55 (s, 2H), 7.49 (d, 2H, J=15.87 Hz), 7.31 (s, 2H), 7.11 (d, 2H, J=8.19 Hz), 6.83 (d, 2H, J=8.19 Hz), 6.37 (d, 2H, J=15.87 Hz), 4.39 (s, 4H).

Example 2

Various ferulic acid dimers were synthesized according to the same procedure as example 1. The results are shown in Table 1.

TABLE 1

| X | N | NMR data |
|---|---|---|
| C | 1 | 9.89 (bs, 2H), 7.49 (d, 2H, J = 15.8 Hz), 7.28 (s 2H), 7.01 (d, 2H, J = 8.1 Hz), 6.75 (d, 2H, J = 8.1 Hz), 6.35 (d, 2H, J = 15.8 Hz), 4.12 (t, 4H, J = 4. Hz), 1.97–2.03(m, 4H), 1.82–1.87 (m, 2H) |
| C | 2 | 9.77(bs, 2H), 7.46 (d, 2H, J = 15.8 Hz), 7.27 (s, 2H), 7.06 (d, 2H, J = 8.2 Hz), 6.77 (d, 2H, J = 8.2 Hz), 6.31 (d, 2H, J = 15.8 Hz), 4.16 (t, 4H, J = 4. Hz), 1.92–2.06 (m, 8H), 1.81–1.88 (m, 2H) |
| O | 1 | 9.47 (bs, 2H), 7.42 (d, 2H, J = 15.8 Hz), 7.25 (s 2H), 7.04 (d, 2H, J = 8.1 Hz), 6.76 (d, 2H, J = 8.1 Hz), 6.30 (d, 2H, J = 15.8 Hz), 4.13 (t, 4H, J = 4. Hz), 3.80 (t, 4H, J = 4.6 Hz) |
| O | 2 | 9.52 (bs, 2H), 7.47 (d, 2H, J = 15.8 Hz), 7.29 (s 2H), 7.08 (d, 2H, J = 8.0 Hz), 6.81 (d, 2H, J = 8.0 Hz), 6.35 (d, 2H, J = 15.8 Hz), 4.14 (t, 4H, J = 4. Hz), 3.80 (t, 4H, J = 4.4 Hz), 3.64 (s, 4H) |
| O | 3 | 9.66 (bs, 2H), 7.45 (d, 2H, J = 15.8 Hz), 7.27 (s 2H), 7.05 (d, 2H, J = 8.1 Hz), 6.79 (d, 2H, J = 8.1 Hz), 6.32 (d, 2H, J = 15.8 Hz), 4.15 (t, 4H, J = 4. Hz), 3.81 (t, 4H, J = 4.5 Hz), 3.78 (t, 4H, J = 4.8 Hz), 3.66 (t, 4H, J = 4.8 Hz) |
| N | 1 | 11.2 (bs, 2H), 9.50 (s, 2H), 7.47 (d, 2H, J = 15. Hz), 7.29 (s, 2H), 7.09 (d, 2H, J = 8.2 Hz), 6.80 (d, 2H, J = 8.2 Hz), 6.33 (d, 2H, J = 15.1 Hz), 4.2 (t, 4H, J = 4.2 Hz), 3.17 (t, 4H, J = 4.2 Hz) |
| N | 2 | 9.48 (bs, 2H), 7.42 (d, 2H, J = 15.8 Hz), 7.25 (s 2H), 7.04 (d, 2H, J = 8.1 Hz), 6.81 (d, 2H, J = 8.1 Hz), 6.29 (d, 2H, J = 15.8 Hz), 4.16 (t, 4H, J = 4. Hz), 3.16 (t, 4H, J = 4.7 Hz), 3.01 (s, 4H) |

Experimental Example 1

Effect of Administration, Learning and Memory-retention Ability on Mice

Four groups of 10 mice aged 4–5 weeks, weighing 20–25 g, were administered with samples dissolved in 1% DMSO and 1% CMC using Sonde once per 1 day(samples: A-reverse phase betaamyloid, B-betaamyloid, C-ferulic acid dimer of example 1 and betaamyloid, D-ferulic acid and betaamyloid). After injection of 1.85 g sample to the celebral ventricle on each of 3 consecutive days, passive avoidance test on days 1 and 2, and Y-maze test on days 3 and 4 following the last injection were conducted. All data attained by the average mean of 10 mice each group.

Injection into the cerebral ventricle was performed according to the method described in Laursen & Belknap, *J. Pharmacol. Methods.* 1986, 16, 355. The tip of a 26 gauge needle fitted in a 50 μl Hamilton syringe was inserted into the bregma of the mouse to a depth of 2.4 mm to administer the samples.

In order to examine the learning and memory-retention ability of a mouse, a passive avoidance test was carried out in accordance with the method described in Song et al., *J.*

Neurochem., 1998, 71, 875. A passive avoidance chamber equipped with a light room and a dark room was prepared, the floor of the dark room being designed to deliver an electrical shock to a test animal. First, a mouse was put in the light room and, upon entering the dark room, it received an electrical shock at 0.25 mA for 1 second. Twenty-four hours after the training, the mouse was put in the light room again and the time it took to enter the dark room was measured as a passive avoidance time. The maximum restriction time was set at 300 seconds, i. e., in cases where the mouse took more than 300 seconds to enter the dark room, the passive avoidance time was determined to be 300 seconds.

Spontaneous alternation behavior of a mouse was examined by a Y-maze test in accordance with the method described in Yamada et al., Eur. J. Pharacolo., 1998, 349, 15. The Y-maze consisted of three arms, shaped like a Y. A test mouse was placed in one of the arms such that it's head faced the arm's terminal, and was allowed to roam freely through the three arms for 8 minutes. The alternation number was determined by counting the number of occasions the mouse entered the three arms sequentially. Spontaneous alternation behavior was determined as the percentage of the alternation number based on the total number of arm entries.

The results are shown in FIG. 1. As can be seen in FIG. 1, the step-through latency (sec) is significantly higher for the mice (C) administered with ferulic acid dimers of formula 1 and beta-amyloid, as compared with the mice (B) administered with beta-amyloid (1–42) only, and thus the learning and memory-retention ability for mice are excellent during the maximum limitation time of 300 seconds.

Experimental Example 2

Oral Toxicity Test of Korea Angelica Root Extract

Twenty female and twenty male Sprague-Dawley rats aged 4 weeks were divided into four groups including 5 female and 5 male rats, after being raised in a vivarium of temperature 22±3° C., relative humidity 50±10%, illumination 150–300 Lux for 1 week.

The ferulic acid dimers prepared in Example 1 was dissolved in corn oil, and the rats of 4 groups were orally administered with the solutions at a dose of 300, 1,000, 3,000 and 10,000 mg/kg one time. For 7 days after administration, changes of general symptoms and occurrence of death were observed. In addition, the rats were killed on day 7 after administration, dissected, and internal organs were examined with unaided eye. From the extract administration day, daily weight changes were measured and thus the weight decrease of animals attributed to ferulic acid dimers was observed.

As a result, $LD_{50}$ values of ferulic acid dimers were found to be 3,722 mg/kg for males, and 2,804 mg/kg for females. All surviving animals were dissected and observed. No pathological changes can be seen with naked eye in case of 1,000 mg/kg or less administered groups. In addition, the body weight was not decreased for the groups administered with 1,000 mg/kg or less.

Experimental Example 3

Protein Selection by Chemical Genomics

In order to study a functional mechanism of ferulic acid dimers, the present inventors conducted an experiment to screen from protein libraries proteins conjugatable with ferulic acid by use the method of chemical genomics. To this end, ferulic acid was immobilized onto a solid substrate and treated with T7 phages having proteins translated from a human brain and cDNA library on their surface to select the proteins bound to the immobilized ferulic acid. For selection of the proteins with the best affinity for ferulic acid, the screening procedure was repeated 3–4 times. Base sequencing of the cDNA selected allowed the amino acid sequences of the corresponding proteins to be inferred. The BLAST search was very useful in finding proteins or corresponding DNA, which have amino acid sequences the most similar to the analyzed sequences of the proteins that were specifically bound to ferulic acid. Of the proteins thus identified, cynuclein and plasophylin attracted particular attention. These two proteins, known to be directly or indirectly associated with formation of intercelluar or intracelluar plaque, were therefore found to be inhibited from forming plaques by ferulic acid. Hence, ferulic acid was identified to effectively treat dementia.

Formulation Example 1

Preparation of Hard Gelatin Capsule Formulation 100 mg of the ferulic acid dimers prepared in Example 1, 45 mg of milk calcium, 122 mg of microcrystalline cellulose, 15 mg of isoflavon, 2.5 mg of ginkgo extract, 2 mg of Zizyphus jujuba extract, 0.25 mg of vitamin $B_1$, 0.3 mg of vitamin $B_2$, 0.0025 mg of vitamin $D_3$ and 2.5 mg of magnesium stearate were mixed thoroughly and filled into a hard gelatin capsule to prepare a hard gelatin capsule formulation.

As described hereinbefore, the ferulic acid dimers represented by formula 1 of the present invention can more effectively inhibit formation of plaque than conventional ferulic acids, thus greatly improving the learning and memory-retention abilities of mice. Also, the ferulic acid dimers can be used to treat dementia and similar diseases, and have fewer side-effects because of no hormone properties of thyroxine, even though administered for long period of time.

The present invention has been described in an illustrative manner, and it is to be understood that the terminology used is intended to be in the nature of description rather than of limitation. Many modifications and variations of the present invention are possible in light of the above teachings. Therefore, it is to be understood that within the scope of the appended claims, the invention may be practiced otherwise than as specifically described.

What is claimed is:

1. Ferulic acid dimers represented by formula 1 and pharmaceutically acceptable salts thereof Formula 1

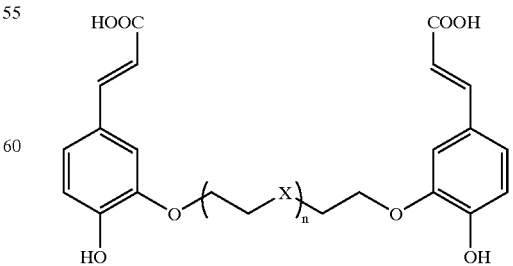

wherein, X is C, O or N, and n is an integer of 0–3.

2. The ferulic acid dimmers and pharmaceutically acceptable salts thereof according to claim 1, wherein X is C or N, and n is an integer of 0–2.

3. The ferulic acid dimmers and pharmaceutically acceptable salts thereof according to claim 1, wherein X is C, and n is 1.

4. The ferulic acid dimmers and pharmaceutically acceptable salts thereof according to claim 1, wherein said alts are inorganic salts or organic salts, and said inorganic salts being selected from the group consisting of sodium salt, potassium salt, magnesium salt and calcium salt, and said organic salts being selected from the group consisting of salts with angelic acid, lysine, ethanolamine, N,N'-dibenzyl ethylenediamine and α-tocopherol.

5. A method for preparing ferulic acid dimmers of claim 1 comprising reacting hydroxybenzaldehyde compound of formula 2 with malonic acid to obtain ferulic acid dimers of formula 1

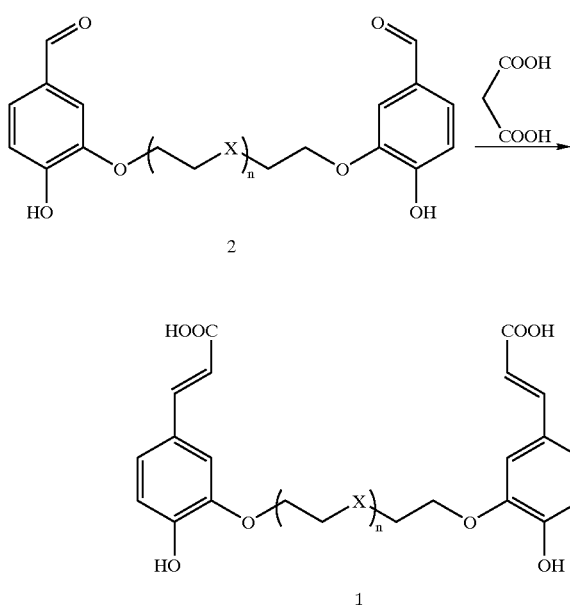

wherein, X is C, O or N, and
n is an integer of 0–3.

6. The method according to claim 5, wherein the reaction is conducted in the presence of pyridine and piperidine.

7. The method according to claim 6, wherein the reaction is conducted at 40–60° C. for 3–5 hours.

8. The method according to claim 5, further comprising the steps of:
reacting hydroxybenzaldehyde compound of formula 4 with ditosyl compound of formula 5 in the presence of base to obtain aldehyde compound of formula 3 (step 1), and
deprotecting the aldehyde compound of formula 3 with an acidic solution to obtain hydroxybenzaldehyde compound of formula 2(step 2)

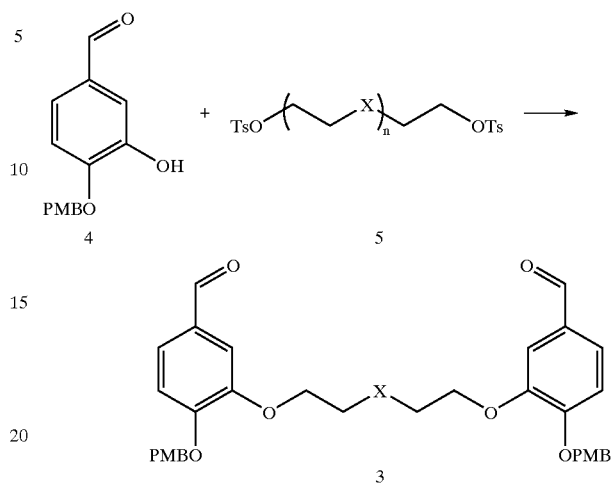

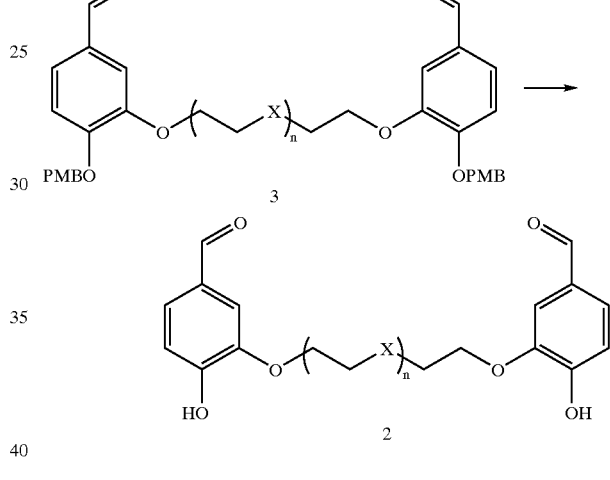

wherein, X is C, O or N, n is an integer of 0–3, and
PMB is paramethoxybenzyl group.

9. The method according to claim 8, wherein the base is LiH, NaH or KH.

10. The method according to claim 8, wherein the acid for deprotection is hydrochloric acid, sulfuric acid or nitric acid.

11. Intermediates for the preparation of the ferulic acid dimmers according to claim 1, represented by formula 2

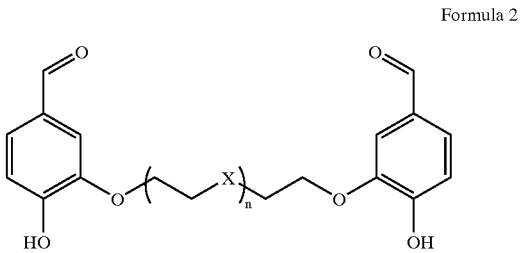

wherein, X is C, N or N, and n is an integer of 0–3.

12. Intermediates for the preparation of the ferulic acid dimmers according to claim 1, represented by formula 3

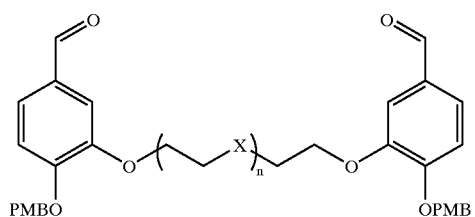

Formula 3 wherein, X is C, N or N; n is an integer of 0–3, and PMB is paramethoxybenzyl group.

13. Pharmaceutical compositions for the treatment of dementia containing ferulic acid dimmers of claim 1 or pharmaceutically acceptable salts thereof as an active ingredient.

14. The pharmaceutical compositions according to claim 13, wherein the pharmaceutical composition further containing carriers and vehicles.

15. The pharmaceutical composition according to claim 13, wherein the dementia is the disease caused by amyloid plague.

* * * * *